US006174875B1

(12) United States Patent
DeFranco et al.

(10) Patent No.: US 6,174,875 B1
(45) Date of Patent: Jan. 16, 2001

(54) BENZOQUINOID ANSAMYCINS FOR THE TREATMENT OF CARDIAC ARREST AND STROKE

(75) Inventors: Donald B. DeFranco; Clifton W. Callaway; Christopher Lipinski; Nianqing Xiao, all of Pittsburgh, PA (US)

(73) Assignee: University of Pittsburgh, Pittsburgh, PA (US)

( * ) Notice: Under 35 U.S.C. 154(b), the term of this patent shall be extended for 0 days.

(21) Appl. No.: 09/282,611

(22) Filed: Apr. 1, 1999

Related U.S. Application Data

(60) Provisional application No. 60/080,605, filed on Apr. 3, 1998.

(51) Int. Cl.$^7$ .................................................. A61K 31/33
(52) U.S. Cl. ........................................................ 514/183
(58) Field of Search ............................................. 514/183

(56) References Cited

U.S. PATENT DOCUMENTS 4,261,989 * 4/1981 Sasaki et al. ........................ 424/244

FOREIGN PATENT DOCUMENTS

| 9408578 | 4/1994 | (WO). |
| 9513820 | 5/1995 | (WO). |
| 9634525 | 11/1996 | (WO). |

OTHER PUBLICATIONS

Scheibel et al, Biochemical Pharmacology, vol. 56, pp. 675–682, 1998.*
Bamberger et al, Molecular and Cellular Endocrinology, vol. 131, pp. 233–240, 1997.*
Conde et al. (1997) J. Mol. Cell. Cardiol. 26:1927.
Hansen et al. (1989) Journal of Immunological Methods 119:203.
Hedge et al. (1995) Journal of Cellular Physiology 165:186.
Katz et al. (1995) J. Cereb. Blood Flow Metab. 15:1032.
Maher et al. (1996) J. Neurosci. 16:6394.
Mailhos et al. (1993) Neuroscience 55:621.
Morimoto et al. (1990) Neuron 5:875.
Morimoto et al. (1992) J. Biol. Chem. 267:21987.
Mosser et al. (1997) Mol. Cell. Biol. 17:5317.
Murakami et al. (1991) Exp. Cell Res. 195:338.
Ohtsuki et al. (1996) Am. J. Physiol. 271:C1085.
Polla et al. (1996) Proc. Natl. Acad. Sci. USA 93:6458.
Schneider et al.(1996) Proc. Natl. Acad. Sci. USA 93:14536.
Schubert et al.(1992) Proc. Natl. Acad. Sci. USA 89:8264.
Schulte et al. (1998) Cell Stress & Chaperones 3:100.
Schulte et al.(1996) Mol. Cell Biol. 16:5839.
Soga et al. (1998) J. Biol Chem. 273:822.
Stebbins et al. (1997) Cell 89:239.
Supko et al. (1995) Cancer Chemother. Pharmacol. 36:305.
Whitesell et al. (1996) Molecular Endocrinology 10:705.
Behl et al., "Glucocorticoids Enhance Oxidative Stress–Induced Cell Death in Hippocampal Neurons in Vitro", *Endocrinology*, vol. 138, No. 1, 1997, pp. 101–106.
Czar et al., "Geldanamycin, a Heat Shock Protein 90–Binding Benzoquinone Ansamycin, Inhibits Steroid–Dependent Translocation of the Glucocorticoid Receptor from the Cytoplasm to the Nucleus", *Biochemistry*, vol. 36, No. 25, 1997, pp. 7776–7785.
Segnitz et al., "The Function of Steriod Hormone Receptors Is Inhibited by the hsp90–specific Compound Geldanamycin*", *J. Biol. Chem.*, vol. 272, No. 30, 1997, pp. 18694–18701.
Staddon et al., "Use of an agent which modulates tyrosine phosphorylation for modulating the permeability of a psychological barrier", *Chem Abstracts*, 132897r, vol. 123, 1995, p. 131.
Welch et al., "Inducement of thermotolerance with benzoquinonoid ansamycins", *Chem. Abstracts*, 42698j, vol. 126, No. 4, 1997, p. 67.

* cited by examiner

*Primary Examiner*—James H. Reamer
(74) *Attorney, Agent, or Firm*—Baker Botts LLP

(57) ABSTRACT

The present invention provides a method of inhibiting oxidative-stress induced cell death in a cell comprising contacting the cell with a composition comprising a benzoquinoid ansamycin. The present invention further provides a method of reducing neurological injury resulting from cardiac arrest or stroke comprising administering to a patient a composition comprising a benzoquinoid ansamycin.

12 Claims, 6 Drawing Sheets

BENZOQUINOID ANSAMYCINS FOR THE TREATMENT OF CARDIAC ARREST AND STROKE

CROSS REFERENCE TO RELATED APPLICATION

This application claims the benefit of U.S. application Ser. No. 60/080,605 filed Apr. 3, 1998, which application is incorporated herein by reference.

STATEMENT REGARDING FEDERALLY SPONSORED RESEARCH OR DEVELOPMENT

This invention was made with United States government support under grant number RO1 CA3037 awarded by the National Institutes of Health. The United States government has certain rights in the invention.

BACKGROUND OF INVENTION

Oxidative stress is considered to be an important causative factor in the onset or progression of neurodegenerative diseases and may contribute to neuronal damage that results from cerebral ischemia (Coyle et al. (1993) *Science* 262:689). Reactive oxygen species (ROS), which are generated as by-products of many metabolic process including monoamine metabolism and arachidonic acid oxidation, may be the principal intracellular mediators of cell death in oxidatively stressed neuronal cells. The damage to various macromolecules by chemical reactions with ROS can initiate an apoptotic program of cell death or lead to cell death by necrosis. Despite the molecular and biochemical details of cellular responses to ROS, it is unclear why neuronal toxicity in response to oxidative stress is often delayed and in some conditions limited to discrete populations of vulnerable neurons.

The neuroprotective effects of a pre-conditioned thermal stress are known and are presumably attributable to the induced synthesis of heat shock proteins (Maihos et al. (1993) *Neuroscience* 55:621). Various members of the heat shock protein family, such as the 70 kDa protein hsp70, play a role in cellular recovery from various forms of stress due to their capacity to act as molecular chaperones (Hartl (1996) *Nature* 381:571). While some studies have detailed the induction of hsp70 mRNA and protein expression in the brain in response to various ischemic insults, the mechanisms responsible for any neuroprotective effects of hsp70 remain enigmatic (Fink et al. (1997) *J. Neurochem.* 68:961). Although thermal stress is clearly an effective means of inducing hsp70 expression, it is not a pharmacologically acceptable approach to the manipulation of heat shock protein expression.

A number of cell culture systems have been exploited to analyze the mechanisms of oxidative stress-induced neuronal death. For example, a mouse hippocampal cell line, HT22, has been developed that is particularly sensitive to glutamate-induced oxidative toxicity (Maher et al. (1997) *J. Neurosci.* 16:6394). The cytotoxic effect of glutamate in HT22 cells is not due to excitotoxic effects of this stimulatory amino acid, as this cell line is devoid of ionotropic glutamate receptors. Rather, glutamate-induced oxidative toxicity of HT22 cells is associated with an inhibition of cysteine transport which subsequently leads to depletion of intracellular glutathione levels and activation of neuronal 12-lipoxygenase. The resulting ROS that are generated by arachidonic acid oxidation in these cells likely activate an apoptotic program of cell death by a number of different mechanisms (Lief al. (1997) *Neuron* 19:453).

Cell culture models, such as HT22 cells, are well suited for studies designed to assess the effectiveness of pharmacological agents in preventing oxidative toxicity. The list of agents that protect cultured neurons from this form of toxicity is quite extensive and includes growth factors, vitamin E, antioxidants, non-steroidal anti-inflammatory agents such as aspirin, and protein kinase inhibitors. The different mechanisms of action of these neuroprotective compounds probably reflects the multitude of cellular processes that contribute to oxidative toxicity. However, since many compounds that provide protection against oxidative toxicity are only effective when given prior to the onset of oxidative stress, their clinical applicability is limited. A need exists for neuroprotective agents that are effective when administered after the onset of oxidative stress, for example after cardiac arrest or stroke.

Geldanamycin, herbimycin A and macbecin are naturally occurring antitumor antibiotics of the benzoquinoid ansamycin class. (DeBoer et al. (1970) *J. Antibiot.* (Tokyo) 23:442, Omura et al. (1979) *J. Antibiot.* 32:255; Ono et al. (1982) *I. Gann.* 73:938.) The main intracellular target of geldanamycin and herbimycin A is the 90 kDa heat shock protein, hsp90. The binding of geldanamycin to hsp90 alters the chaperoning activity of hsp90 and, among other effects, leads to induction of the 70 kDa heat shock protein, hsp70. (Whitesell et al. (1996) *Mol. Endocrinol.* 10:705; Morimoto et al. *J. Biol. Chem.* 267:21987; Wu (1995) Rev. Cell *Dev. Biol.* 11:441.)

In particular, herbimycin A and geldanamycin have been found to induce hsp70 expression in fibroblasts (Murakami et al. (1991) *Exp. Cell Res.* 195:338; Hedge et al. (1995) *J. Cell. Physiol.* 165:186), a myogenic cell line, and rat cardiomyocytes in culture (Conde et al. (1997) *J. Mol. Cell. Cardiol.* 26:1927). Conde et al. disclose that pretreatment of myogenic H9c2 cells and cardiomyocytes with herbimycin or geldanamycin resulted in overexpression of heat shock proteins and conferred protection against simulated ischemia.

A requirement for pretreatment limits the practical therapeutic utility of agents for the treatment of cardiac arrest or stroke. The present invention, by providing a method of preventing damage resulting from cardiac arrest or stroke in which the agent is administered following the onset of the damaging insult, has significant clinical applicability.

SUMMARY OF THE INVENTION

The present invention provides a method of inhibiting cell death induced by oxidative stress in a cell comprising contacting the cell with an cell-death-inhibiting effective amount of a composition comprising a benzoquinoid ansamycin. In a preferred embodiment the cell is a neuronal cell and the benzoquinoid ansamycin is geldanamycin or herbimycin A.

The present invention further provides a method of reducing neurological injury resulting from cardiac arrest or stroke comprising administering to a patient suffering from cardiac arrest or stroke a composition comprising an effective amount of a benzoquinoid ansamycin. In a preferred embodiment the benzoquinoid ansamycin is geldanamycin or herbimycin A.

In another embodiment, the present invention provides an article of manufacture comprising a packaging material and a pharmaceutical composition contained within the packaging material, wherein the pharmaceutical composition comprises a benzoquinoid ansamycin, and wherein the packaging material comprises a label that indicates that the composition can be used to reduce neurological injury resulting from cardiac arrest or stroke.

DETAILED DESCRIPTION OF THE INVENTION

Figure 1:
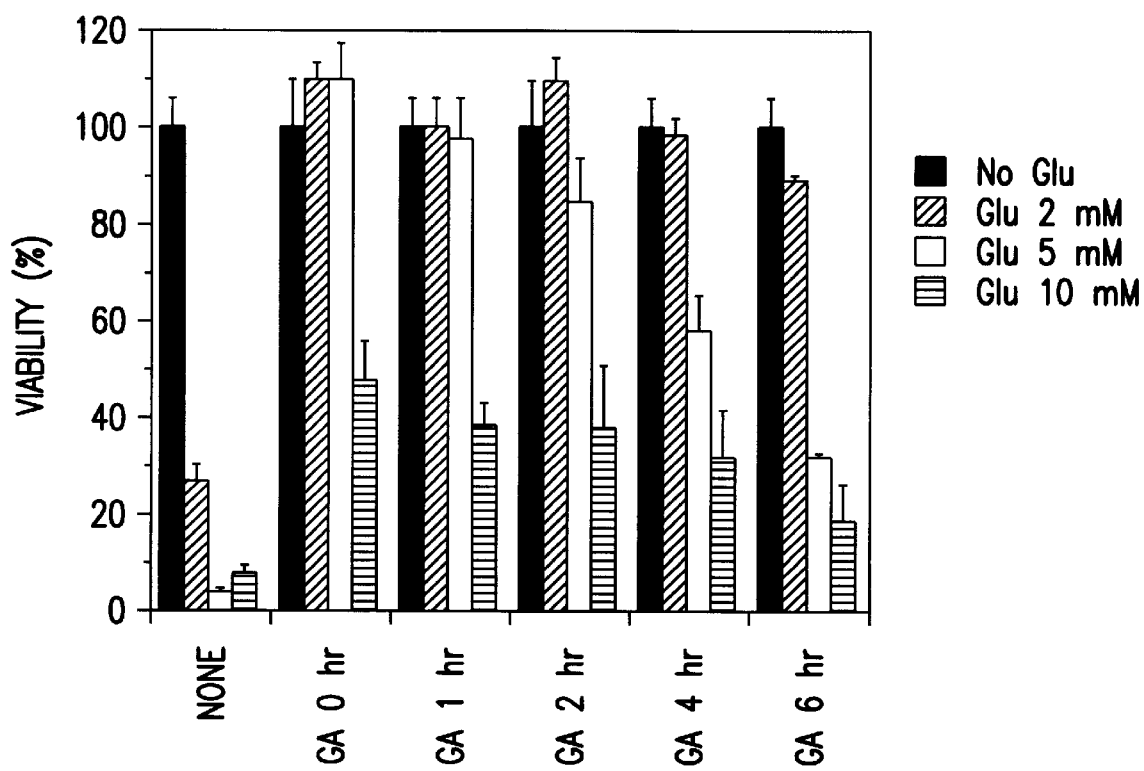
FIG. 1 is a graph depicting viability of cells treated with geldanamycin simultaneously with or subsequent to treatment with glutamate.

The benzoquinoid ansanycins are compounds having a benzoquinone moiety, an ansa ring, and a carbamate noiety. The benzoquinoid ansamycins may be represented by the general formula:

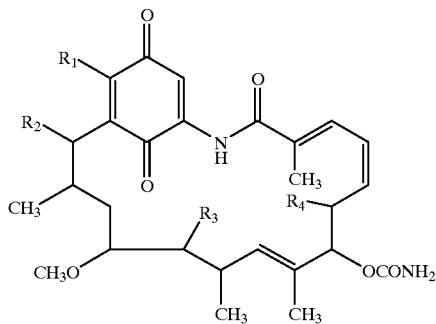

I

Naturally occurring benzoquinoid ansamycins include geldanamycin ($R_1$=$OCH_3$; $R_2$=H; $R_3$=OH; $R_4$=$OCH_3$), herbimycin A ($R_1$=H; $R_2$=$OCH_3$; $R_3$=$OCH_3$; $R_4$=$OCH_3$) and macbecin I ($R_1$=H; $R_2$=$OCH_3$; $R_3$=$OCH_3$; $R_4$=$CH_3$). Geldanamycin and herbimycin A are commercially available.

It has been discovered in accordance with the present invention that compounds of the benzoquinoid ansamycin class are capable of inhibiting cell death induced by oxidative stress. Accordingly, the present invention provides a method of inhibiting cell death induced by oxidative stress in a cell comprising contacting a cell undergoing oxidative stress with a cell death-inhibiting effective amount of a composition comprising a benzoquinoid ansamycin.

Oxidative stress in a cell may result from various conditions characterized by an increased oxidative burden, including for example ischemia, reperfusion, sepsis, and acute inflammation. In a preferred embodiment of the present invention, the cell is a neuronal cell and oxidative stress results from cardiac arrest or stroke.

In accordance with the present invention, inhibition of cell death is defined as a statistically significant ($P<0.05$) reduction in the number of cells undergoing cell death. Cell death may be measured by methods known in the art, including for example DNA laddering, terminal deoxynucleotidyltransferase-mediated dUTP nick end labeling (TUNEL) assays, and DNA dye binding assays. In DNA laddering, characteristic nucleosome-sized cytoplasmic DNA indicates the presence of fragmented cytoplasmic DNA in the cytoplasm, and is used as a marker for cell death. In TUNEL staining of cell monolayers, fluorescein-linked digoxigenin antibodies are used to detect the location of deoxyuridine residues that have been attached by terminal transferase to free 3' OH groups of DNA. Brightly fluorescing cells indicate the presence of fragmented DNA. In DNA dye binding assays, extranuclear staining with DNA-intercalating dye such as Hoechst 33258 is a marker for cell death.

In a preferred embodiment, the benzoquinoid ansamycin is geldanamycin or herbimycin A. The terms geldanamycin and herbimycin A, as used herein, include analogues thereof that are capable of binding to hsp 90 and inhibiting cell death induced by oxidative stress. Compositions useful in the present method preferably comprise a cell death-inhibiting effective amount of geldanamycin and a carrier. A cell death-inhibiting effective amount is that amount that inhibits cell death by any of the above-described assays for cell death. The term carrier as used herein includes any and all solvents, diluents, dispersion media, antibacterial and antifungal agents, microcapsules, liposomes, cationic carriers, isotonic and absorption delaying agents, and the like.

A cell undergoing oxidative stress may be contacted with the composition of the invention by known methods including direct application to the cell, by intravenous, subcutaneous, intramuscular, intraperitoneal, and intraepidural injection, by topical administration, by inhalation, or by depot injections or erodible implants. In a preferred embodiment the cell is a neuronal cell, and the neuronal cell is contacted with the composition by direct application. In another preferred embodiment, the cell is contacted with the composition after the onset of the oxidative stress, and preferably within about two hours of the onset of the oxidative stress.

It has been further discovered in accordance with the present invention that the administration of a composition comprising a benzoquinoid ansamycin to a patient suffering from cardiac arrest or stroke results in a reduction in neurological injury associated with cardiac arrest or stroke. Accordingly, the present invention provides a method of reducing neurological injury resulting from cardiac arrest or stroke comprising administering to a patient suffering from cardiac arrest or stroke a composition comprising an effective amount of a benzoquinoid ansamycin.

In a preferred embodiment, the benzoquinoid ansamycin is geldanamycin or herbimycin A. An effective amount is defined herein as an amount effective to prevent or reduce neurological injury generally associated with cardiac arrest or stroke. Prevention or reduction of neurological injury may be assessed by scoring with standardized behavioral tests or by direct examination of brain histology post-mortem.

The compositions preferably contain geldanamycin or herbimycin A and a carrier as defined above, and are administered by known routes as described above. In a preferred embodiment the composition is administered by intravenous infusion.

The compositions of the present invention reduce neurological injury when administered after the onset of cardiac arrest or stroke. The compositions are preferably administered within about two hours after the onset of cardiac arrest or stroke, and more preferably within about one hour, and most preferably within about five minutes after the onset of cardiac arrest or stroke.

The formulation of pharmaceutical compositions is generally known in the art and reference can conveniently be made to Remington's Pharmaceutical Sciences, 17th ed., Mack Publishing Co., Easton, Pennsylvania. Formulation of benzoquinoid ansamycins for use in present methods must be stable under the conditions of manufacture and storage and must also be preserved against the contaminating action of microorganisms such as bacteria and fungi. Prevention against microorganism contamination can be achieved through the addition of various antibacterial and antifungal agents.

The pharmaceutical forms of benzoquinoid ansamycins suitable for administration include sterile aqueous solutions or dispersions and sterile powders for the extemporaneous preparation of sterile injectable solutions or dispersions. In all cases, the form must be sterile and may be fluid to the extent that easy syringability exists. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants, or vegetable oils. Sterilization can be accomplished by an art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject compounds is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

The subject compounds are thus compounded for convenient and effective administration in pharmaceutically effective amounts with a suitable pharmaceutically acceptable carrier and/or diluent in a therapeutically effective dose.

As used herein, the term "pharmaceutically acceptable carrier and/or diluent" includes any and all solvents, dispersion media, antibacterial and antifungal agents, microcapsules, liposomes, cationic lipid carriers, isotonic and absorption delaying agents and the like which are not incompatible with the active ingredients. The use of such media and agents for pharmaceutical active substances is well known in the art. Supplementary active ingredients may also be incorporated into the compositions and used in the methods of present invention.

The precise therapeutically effective amount of the benzoquinoid ansamycin to be used in the methods of this invention applied to humans can be determined by the ordinary skilled artisan with consideration of individual differences in age, weight, extent of disease and condition of the patient. It can generally be stated that the pharmaceutical preparation of the present invention should be preferably administered in an amount of at least about 1 mg/kg per infusion dose, and more preferably in an amount up to about 10 mg/kg per dose, or at a dose that achieves a serum concentration of at least about 0.1 $\mu$g/ml.

It is especially advantageous to formulate parenteral compositions in dosage unit form for ease of administration and uniformity of dosage. Dosage unit form as used herein refers to physically discrete units suited as unitary dosages for the mammalian subjects to be treated, each unit containing a predetermined quantity of active material calculated to produce the desired therapeutic effect in association with the required pharmaceutical carrier. The specification for the novel dosage unit forms of the invention are dictated by and directly depend upon the unique characteristics of the active material, and the limitations inherent in the art of compounding such an active material for the treatment of neurological injury resulting from cardiac arrest or stroke.

The principal active ingredient is compounded for convenient and effective administration in effective amounts with a suitable pharmaceutically acceptable carrier in dosage unit form as hereinabove disclosed. In the case of compositions containing supplementary active ingredients, the dosages are determined by reference to the usual dose and manner of administration of the ingredients.

The present invention further provides an article of manufacture comprising a packaging material and a pharmaceutical composition contained within the packaging material, wherein the pharmaceutical composition comprises a benzoquinoid ansamycin, and wherein the packaging material comprises a label that indicates that the composition can be used to reduce neurological injury resulting from cardiac arrest or stroke. In a preferred embodiment the benzoquinoid ansamycin is geldanamycin or herbimycin A. The pharmaceutical compositions may be prepared as described hereinabove. The packaging material may comprise glass, plastic, metal, or any other suitable inert material that does not react with any of the ingredients contained therein.

All references cited herein are incorporated herein in their entirety.

The following examples further illustrate the present invention and are not intended in any way to limit the scope of the invention.

EXAMPLE 1

Geldanamycin induces hsp 70 expression in HT-22 cells

Cells of the HT22 hippocampal cell line (obtained from Dr. David Schubert, The Salk Institute for Biological Studies, LaJolla, Calif. 92037) were grown in Dulbecco's minimum essential medium (DMEM) (Gibco-BRL) with 10% fetal bovine serum (Atlanta Biologicals) overnight, then treated with 5 mM glutamate and/or 0.1 $\mu$g/ml geldanamycin (GA)( obtained from Drug Synthesis and Chemistry Branch, Developmental Therapeutics Program, Division of Cancer Treatment, National Cancer Institute) for various lengths of time (0, 3, 6, 9, and 12 hours). This concentration of GA was chosen since it had been found to induce hsp70 expression in other cells (Conde et al., supra). Furthermore, induction of hsp70 protein levels in HT22 cells was not significantly enhanced at higher doses of GA.

Cells were harvested and lysed by sonication in 0.25 M Tris-HCl, pH 7.5 and lysates clarified by centrifugation at 14,000 rpm for 10 minutes at 4° C. Equivalent amounts of lysate protein (5 $\mu$g) were used for Western blot analysis as described by Xiao et al. (1997) *Mol. Endocrinol.* 11: 1365. The inducible form of the 70 kDa heat shock protein, hsp70, was uniquely detected using the SPA-810 monoclonal antibody (StressGen). GA induction of hsp70 was evident within 3 hours of GA treatment, was maximal upon 9 hours of GA treatment, and persisted for at least 12 hours in the presence of GA. The introduction of hsp70 by GA in HT22 cells was as effective as a 60 minute 42° C. heat shock. As steady state levels of hsp90 in HT22 cells were not affected by this GA treatment, this compound does not generally up-regulate the expression of all members of the heat shock protein family. In fact, it is known that GA treatment in other cultured cells typically leads to the selective degradation of hsp90-associated signaling molecules.

In contrast to the effects of GA and thermal stress, hsp70 was not induced in HT22 cells which were subjected to oxidative stress as a result of treatment with 5 mM glutamate. This oxidative stress in HT22 cells ultimately culminates in cell death. Since GA treatment was still able to induce hsp70 in the presence of 5 mM glutamate, the pathway leading to hsp70 induction in HT22 cells was not immobilized by oxidative glutamate toxicity. This example demonstrates that hsp70 levels are induced by GA, and that GA-induced hsp70 levels are maintained in the presence of 5 mM glutamate for up to 12 hours in HT22 cells.

EXAMPLE 2

Geldanamycin Protects HT22 Cells from Glutamate-Induced Cytotoxicity

HT22 cells were seeded on 60 mm tissue culture dishes at 300,000 cells per dish and grown overnight. Cells were then incubated in the presence of 5 mM glutamate for 20 hours. 5 Geldanamycin (0.1 $\mu$g/ml) was added either at the same time, or 1, 2 or 6 hours after the addition of glutamate. Phase contrast images demonstrated that treatment of HT22 cells with 0.1 $\mu$g/ml GA led to protection from glutamate-induced oxidative toxicity. After 24 hours of glutamate treatment, extensive cell death was visible both by inspection of HT22 cell cultures under light microscopy and as assessed by trypan blue staining. Treatment with GA alone appeared to reduce HT22 cell growth rate, but did not lead to cell death when assessed after 24 hours. These results demonstrate that Geldanaamycin protects HT22 cells from glutamate-induced cytotoxicity, even when added after glutamate. In order to provide a more accurate assessment of glutamate-induced oxidative toxicity, the ability of HT22 cells to metabolize 3-(4,5-dimethyldiazol-2-yl)-2,5-diphenyl tetrazolium bromide (MTT) was assayed. The reduction of this dye by viable cells can easily be detected spectrophotometrically as described by Mosman (1983) *J. Immunol. Methods* 65:55 with reduced HT22 cell viability directly correlated with decreased metabolism of MTT (Shubert et al. (1992) *Proc. Natl. Acad. Sci. USA* 89:8264). HT22 cells were seeded on 96-well plates at 5,000 cells per well and grown for 12 hours. Cells were then treated with 2 mM, 5 mM or 10 mM concentrations of glutamate. Geldanamycin (GA) (0.1 $\mu$g/ml) or herbimycin A (Herb) (obtained from Sigma Chemical Corporation, St. Louis, Mo.) (0.5 $\mu$g/ml) was added either at the same time as glutamate, or at 1, 2, 4 or 6 hours after the addition of glutamate. After a total incubation period of 20 hours, cell viability was measured using an MTT assay as described by Li et al. (1997) *Neuron* 19:453. Briefly, 10 $\mu$l of MTT solution (5 mg/ml) was added to each well and cells incubated for an additional 4 hours. 100 $\mu$l of solubilization solution (50% dimethylformamide and 20% SDS, pH 4.8) was added and left on the cells 5 overnight, after which light absorption at 570 nm was measured. Values (% Viability) represent the average of quadruplicate (FIG. 1) or triplicate (FIG. 2) determinations±S.D. Similar results were obtained in a replicate experiment. Cell viability was expressed relative to control cells treated with GA or Herb alone.

Figure 2:
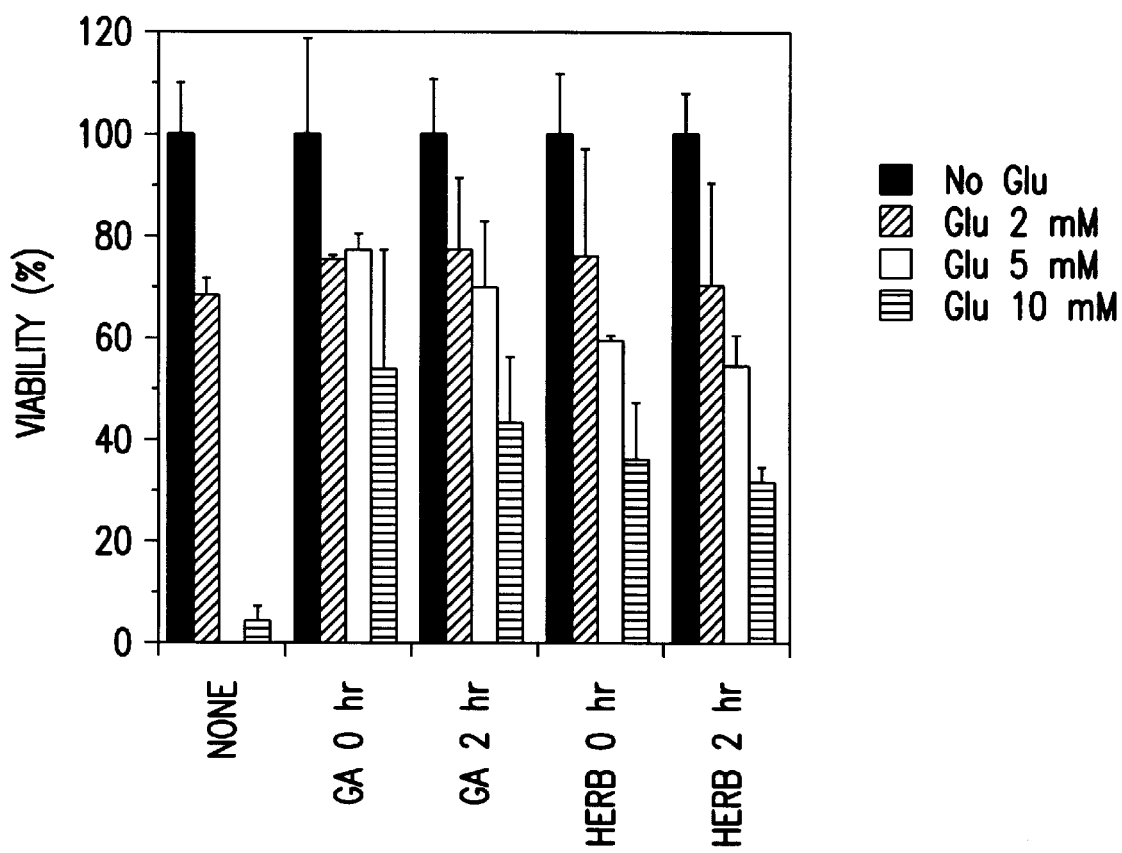
FIG. 2 is a graph depicting viability of cells treated with geldanamycin or herbimycin A simultaneously with or subsequent to treatment with glutamate.

As shown in FIG. 1, 0.1 $\mu$g/ml GA provided effective protection in HT22 cells against cytotoxic effects observed in the presence of 2 and 5 mM glutamate. GA still protected HT22 cells from toxicity that resulted from a 10 mM glutamate treatment, but it was less effective at this higher dose of glutamate. Herbimycin A, another benzoquinoid ansamycin closely related to GA, also protected HT22 cells from the glutamate-induced oxidative toxicity (FIG. 2).

As shown in FIG. 1, GA retained its capacity to protect HT22 cells from oxidative stress, even if given after the addition of glutamate. The ability of GA, given following glutamate treatment, to protect HT22 cells from glutamate-induced oxidative toxicity diminished over time but was still apparent 6 hours after cells were initially exposed to 2 or 5 mM glutamate (FIG. 1). Thus, unlike the animal models of pre-conditioned thermal stress (see e.g., Mailhos et al. (1993) *Neuroscience* 55:621), GA-induction of hsp70 can be associated with protection against cell death in HT22 cells, even if hsp70 induction follows the initiation of glutamate-induced oxidative toxicity.

EXAMPLE 3

Glutamate-induced Depletion of Glutathione Levels is not Reversed by Geldanamycin Treatment Cellular glutathione (GSH) levels were measured in HT22 cells as described previously by Kane (1993) *Science* 262:1274. Briefly, HT22 cells were seeded onto 96-well plates at 20,000 cells per well and grown overnight. Cells were then treated with 5 mM glutamate (Glu) and/or 0.1 $\mu$g/ml geldanamycin (GA) for 2, 4, 6 or 8 hours. Monochlorobimane was added to 40 $\mu$M and following an additional 30 minutes of incubation, fluorescence at 460 nm in response to excitation at 395 mn was measured using a Perkin Elmer fluorescence plate reader. Values represent the average of triplicate experiments±S.D.

Figure 3:
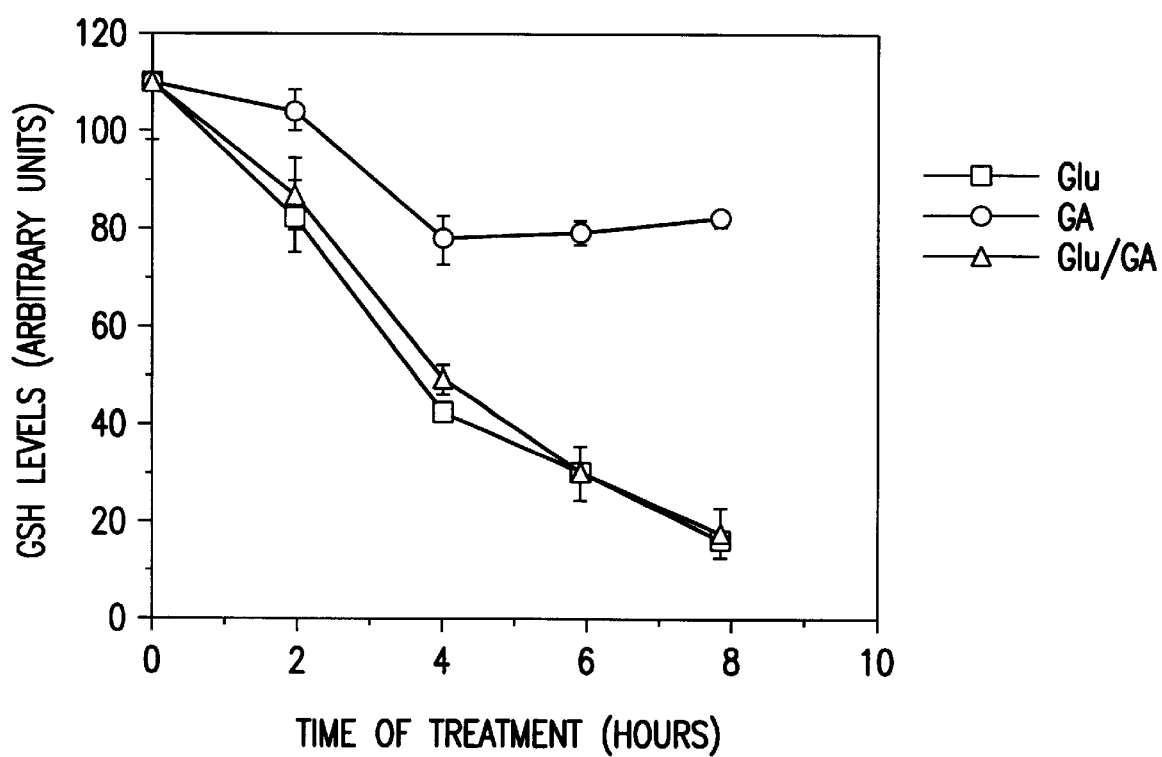
FIG. 3 is a graph depicting geldanamycin on glutamate-induced reduction in glutathione levels.

It had been suggested that an early event in glutamate-induced oxidative toxicity in HT22 cells is the depletion of cellular glutathione levels which reflects intracellular oxidative stress (Li et al., supra). In the present example, the reported protracted time course of glutathione depletion in glutamate-treated HT22 cells has been confirmed. (FIG. 3.) However as also shown in FIG. 3, GA treatment, while protective against oxidative glutamate toxicity in HT22 cells, did not lead to recovery of glutathione levels. Thus, the protective effects of GA are not due to recovery of the cellular reducing capacity that is diminished upon glutamate-induced oxidative stress. There are other examples in which protection from neuronal death that results from oxidative stress was not correlated with the recovery of depleted cellular glutathione (see, e.g., Murphy et al. (1989) *Neuron* 2: 1547). Thus, GA must prevent initiation of a program of delayed cell death in HT22 cells that follows glutathione depletion.

EXAMPLE 4

Geldanamycin Inhibits Glutamate-Induced Apoptosis

Since oxidative glutamate toxicity in HT22 cells has the characteristics of programmed cell death, the present example was performed to determine whether the protective effects of GA result from a disruption in the apoptotic program. HT22 cells were treated with 5 mM glutamate (Glu) for 20 hours. 0.1 $\mu$g/ml geldanamycin (GA) was added either at the same time as glutamate, or 1, 2 or 6 hours after the addition of glutamate. Controls included HT22 cells not treated with Glu or GA and cells treated with GA alone. Genomic DNA was prepared as described by Ausubel et al.; eds, *Current Protocols in Molecular Biology*, Vol. 2 John Wiley and Sons, Inc., Boston, 1994.

Internucleosomal DNA cleavage, a hallmark of apoptosis, was detected in HT22 cells following a 20 hour treatment with glutamate. Untreated HT22 cells, or cells treated with GA alone, were not subjected to this type of characteristic genomic DNA cleavage. Consistent with its protective effects revealed by cell morphology and MTT assays (Example 2), GA was able to block glutamate-induced internucleosomal DNA cleavage in HT22 cells. Based upon the results of the DNA cleavage and glutathione measurements, this example demonstrates that GA acts to prevent oxidative stress-induced apoptosis in HT22 cells.

EXAMPLE 5

Geldanamycin Induces hsp70 Expression In Rat Brain

Figure 5A:
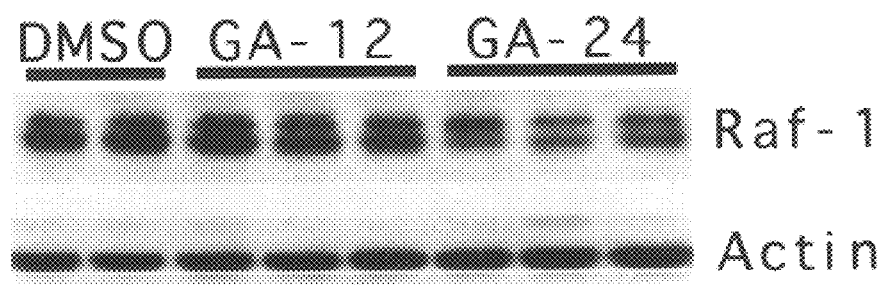
FIGS. 5A and B are Western blots demonstrating the induction of hsp70 and down-regulation of raf-1 in rat brain following intracranial injection of geldanamycin.
Figure 5B:

Geldanamycin was delivered to rat brain by intracranial ventricular (icv) injection as follows. Rats were stereotaxically fitted with 4 mm×22 gauge guide cannulae directed at the lateral ventricle (AP-2.0, ML+2.0). Three days later, geldanamycin (20 µg in 10 ml of dimethyl sulfoxide (DMSO)) or DMSO vehicle was injected over 60 seconds. The injector was removed and replaced with a stylet. At 12 or 24 hours after injection, hippocampi were isolated from which whole cell extracts were prepared and subjected to Western blot analysis to visualize raf- 1 and actin, or hsp70. Negative and positive control protein samples for hsp70 were prepared from untreated or heat shocked HT22 cells. Western blot analysis is depicted in FIGS. 5A and 5B in which the (−) and (+) lanes refer to the negative and positive control samples. As depicted therein, administration of geldanamycin resulted in increased expression of hsp70 and decreased expression of the raf-1 proto-oncogene. These data demonstrate the biochemical effect of geldanamycin in vivo, and the correlation of geldanamycin's effects in vivo and in vitro.

EXAMPLE 6

Pharmacokinetic Analysis of 17-Allylaminogeldanamycin 17-allylaminogeldanamycin (17-AAG) (60 mg/kg) was administered to CD2F1 mice by intravenous (iv) injection. Brain levels of 17-AAG were determined at various time points after administration. As shown in the graph at FIG. 6, 17-AAG accumulated in brain tissue within minutes following iv injection of 60 mg/kg. 17-AAG levels remained fairly constant over the first few hours after iv injection, but then declined over the next 16–18 hours to approximately 10% of peak values. At one day following iv injection (60 mg/kg) 17-AAG levels in brain (i.e., 0.1 µg/g) are comparable to the levels used in cell culture (i.e., 0.1 µg/ml) to bring about desired biochemical effects and protection from oxidative toxicity.

EXAMPLE 7

Improved Neurological Outcome in Rats Treated with Geldanamycin After Cardiac Arrest A rat model of cardiac arrest was used to test geldanamycin's effects in a clinically relevant setting of acute neurological injury. In rats, asphyxia produces circulatory arrest that can be reversed by mechanical ventilation and external chest compression (Katz et al. (1995) *J. Cereb. Blood Flow Metab.* 15:1032). Rats subjected to eight minutes of asphyxia and resuscitation exhibit behavioral and histological cerebral injury. Antioxidant depletion in the hippocampus during early reperfusion after asphyxial cardiac arrest indicates that this model produces a significant oxidative stress in the brain (Callaway et al. (1996) *Acad. Emerg. Med.* 3:544). Meaningful behavioral scores that predictable detect neurological deficits which closely mimic the types of deficits observed in patients that recover from cardiac arrest have been developed. Animal protocols were approved by the Institutional Animal Care and Use Committee of the University of Pittsburgh. Male Sprague-Dawley rats weighing 318±17 gm (Harlan, Indianapolis, Ind.) were anesthetized with 0.8% halothane in oxygen, endotracheally intubated using a 14 gauge angiocath, and mechanically ventilated using a Harvard rodent ventilator (0.9 cc/kg, 40 respirations/min). Blood pressure and arterial blood gases are monitored via a femoral arterial catheter (PE-50 tubing, IntraMedic), and drugs administered via a femoral venous catheter (PE-50). Tympanic temperature was maintained at 36.9±0.2° C. by manipulating an overhead 100 W lamp. After chemical paralysis with 2 mg/kg vecuronium and reducing the fraction of inspired oxygen to 0.21 (room air) mechanical ventilation was discontinued at end-expiration. Cardiac arrest (mean arterial pressure <10 mmHg) reliably occurred within 180 seconds. After 8 minutes of asphyxia, the ventilator was restarted at 70 respirations/minute, chest compressions were performed at a rate of 200/minute and 0.005 mg/kg epinephrine with 1 mEq/kg sodium bicarbonate administered intravenously. After return of spontaneous circulation, GA (1.0 mg/kg) or vehicle (DMSO 1 ml/kg) were administered intravenously over 60 seconds. After 60 minutes, arterial and venous lines were removed. The rats were extubated and returned to cages for behavioral observation. Standardized neurological deficit scores developed for this model by Katz et al., supra, were obtained at 24, 48 and 72 hours. The neurological deficit scores consist of five components: consciousness and respiration, cranial nerve function, motor function, sensory function, and coordination.

Figure 4:
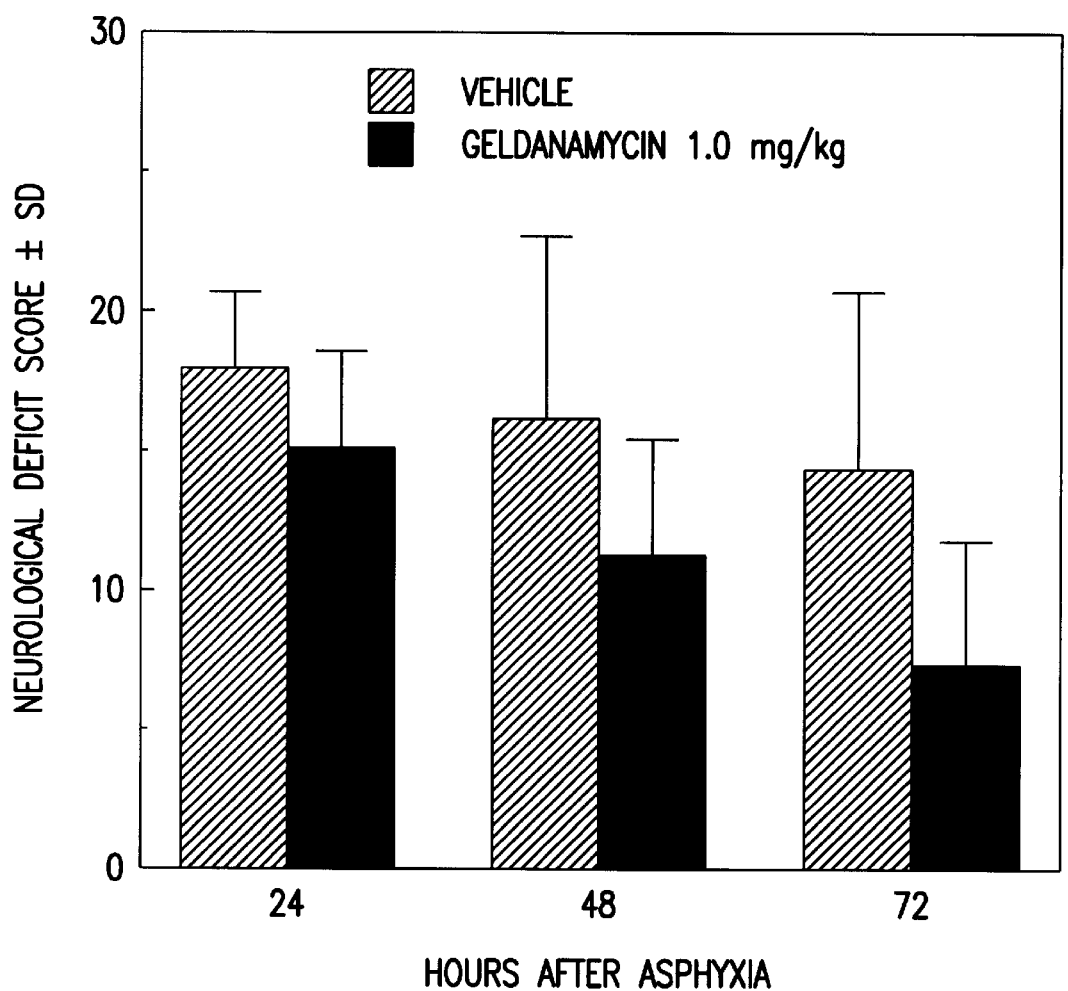
FIG. 4 is a graph of neurological deficit scores in rats treated with geldanamycin or control after asphyxial-induced cardiac arrest.

As shown in FIG. 4, neurological deficit scores were lower in rats treated with GA (n=5) than in rats treated with vehicle (n=5) (Kruskal-Wallace Chi-square=6.54, p<0.05). Baseline arterial blood gases (pH 7.40±0.04, $pCO_2$ 40±5, $pO_2$ 409±68) and blood g levels (112±26 mg/dl) did not differ between groups. Baseline arterial blood gases also did not differ at 10, 30 and 60 minutes after resuscitation. Base deficits <5 mEq/1 were treated with graded doses of sodium bicarbonate. These data indicate that physiological variables did not differ between groups during the resuscitation phase, indicating that the improvement in neurological outcome did not result from acute changes in hemodynamic or metabolic status. Based upon previous pharmacokinetic data (Supko et al. (1995) *Cancer Chemoter. Pharmacol.* 36:305), it was estimated that the dose of GA employed would result in serum concentrations of greater than 0.1 µg/ml during the first 60–120 minutes after reperfusion. These data indicate that the GA-induced improvements in survival of HT22 cells after oxidative stress are relevant to acute neuronal dysfunction in vivo.

The foregoing results therefore provide a demonstration of a pharmacological treatment that, when applied following the damaging insult, is neuroprotective in a cultured cell line, and improves neurological outcome in intact animals.

We claim:

1. A method of inhibiting cell death induced by oxidative stress in a cell comprising contacting said cell with a cell death-inhibiting effective amount of a benzoquinoid ansamycin.

2. The method of claim 1 wherein said benzoquinoid ansamycin is geldanamycin.

3. The method of claim 1 wherein said benzoquinoid ansamycin is herbimycin A.

4. The method of any one of claims 1–3 wherein said cell is a neuronal cell.

5. A method of reducing neurological injury resulting from cardiac arrest or stroke comprising administering to a patient suffering from cardiac arrest or stroke a composition comprising an effective amount of a benzoquinoid ansamycin.

6. The method of claim 5 wherein said benzoquinoid ansamycin is geldanamycin.

7. The method of claim 5 wherein said benzoquinoid ansamycin is herbimycin A.

8. The method of any of claims 5–7 wherein said composition is administered within two hours of cardiac arrest or stroke.

9. The method of any of claims 5–7 wherein said composition is administered by intravenous infusion.

10. A article of manufacture comprising a packaging material and a pharmaceutical composition contained within said packaging material, wherein said pharmaceutical composition comprises a benzoquinoid ansamycin, and wherein said packaging material comprises a label that indicates that said composition can be used to reduce neurological injury resulting from cardiac arrest or stroke.

11. The article of manufacture of claim 10 wherein said benzoquinoid ansamycin is geldanamycin.

12. The article of manufacture of claim 10 wherein said benzoquoinoid ansamycin is herbimycin A.

* * * * *

UNITED STATES PATENT AND TRADEMARK OFFICE
CERTIFICATE OF CORRECTION

PATENT NO. : 6,174,875 B1  
DATED : January 16, 2001  
INVENTOR(S) : DeFranco et al.

Figure 6:
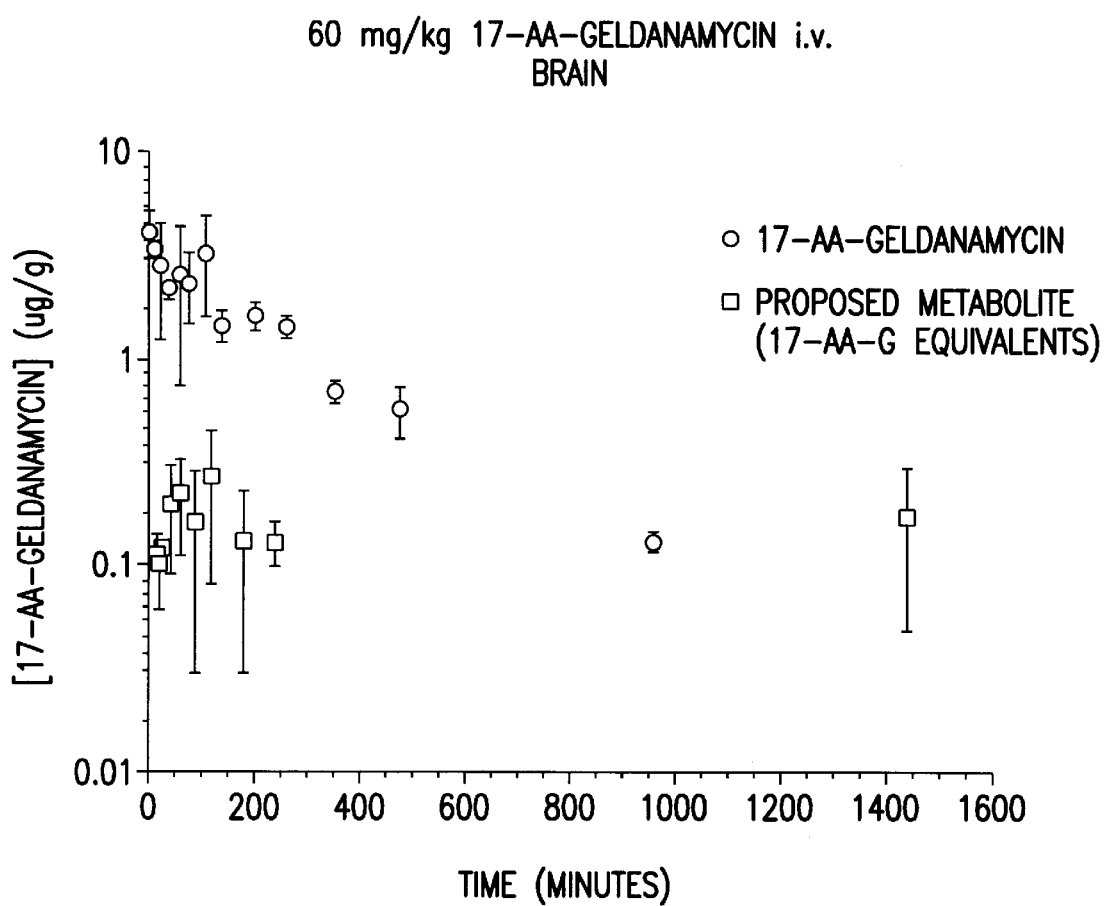
FIG. 6 is a graph depicting the accumulation of 17-allylaminogeldanamycin in mouse brain following intravenous administration.

It is certified that error appears in the above-identified patent and that said Letters Patent is hereby corrected as shown below:

Drawings,  
Figure 6, "(ug/g)" should read -- ($\mu$g/g) --

Column 1,  
Line 67, "al." should read -- et al. --

Column 3,  
Line 14, "asphixial-" should read -- asphixially --  
Line 26, "ansanycins" should read -- ansamycins --  
Line 27, "noiety." should read -- moiety. --

Column 7,  
Line 20, "5" should be deleted.  
Line 30, "Geldanaamycin" should read -- geldanamycin --

Column 11,  
Line 8, "A" should read -- An --

Column 12,  
Line 8, "benzoquoinoid" should read -- benzoquinoid --

Signed and Sealed this

Twenty-ninth Day of January, 2002

*Attest:*

JAMES E. ROGAN  
*Attesting Officer*   *Director of the United States Patent and Trademark Office*